United States Patent [19]
Weiler

[11] Patent Number: 5,462,200
[45] Date of Patent: Oct. 31, 1995

[54] THREADED CAP WITH CONTROLLED ORIFICE LINER FOR PIERCING A SEALED CONTAINER

[75] Inventor: Gerhard H. Weiler, South Barrington, Ill.

[73] Assignee: Automatic Liquid Packaging, Inc., Woodstock, Ill.

[21] Appl. No.: 184,660

[22] Filed: Jan. 21, 1994

[51] Int. Cl.⁶ ..................................................... B67D 5/00
[52] U.S. Cl. .............................. 222/83; 222/90; 222/420
[58] Field of Search ............................. 222/212, 83, 89, 222/90, 91, 420

[56] References Cited

U.S. PATENT DOCUMENTS

3,454,196  7/1969  Hazard .
3,580,423  5/1971  Gilman ................................. 222/90 X
3,813,009  5/1974  Lenz ........................................... 222/90
4,624,393  11/1986  Lopez ..................................... 222/89 X
4,723,687  2/1988  Kutterer .
5,228,592  7/1993  Pellerano ................................. 222/83
5,297,697  3/1994  Boring ..................................... 222/83

Primary Examiner—Gregory L. Huson
Attorney, Agent, or Firm—Olson & Hierl, Ltd.

[57] ABSTRACT

A hermetically sealed container is provided with an overcap and a metamorphic spike carried therein for piercing a membrane on the container. The metamorphic spike is hollow and provides a liner that defines a controlled dispensing passageway. The spike pierces the membrane and is retained within the membrane after the overcap is removed so as to provide a controlled dispensing orifice for the container. The overcap can be reapplied to the container to seal the dispensing orifice.

16 Claims, 4 Drawing Sheets

THREADED CAP WITH CONTROLLED ORIFICE LINER FOR PIERCING A SEALED CONTAINER

TECHNICAL FIELD

This invention relates to a dispensing orifice assembly for use on a container having an access port thereto defined by a boss and sealed by a pierceable membrane. More particularly, the invention relates to an improved orifice assembly for providing a dispensing orifice of a predetermined size.

BACKGROUND OF THE INVENTION

Hermetically sealed containers with unitary closures are known. Such containers typically have a body portion, a neck portion or boss defining an access port, and a closure structure to close and seal the port.

It is also known to provide such containers with means for permitting the containers to be opened by puncturing the closure seal to form a dispensing orifice. See, for example, U.S. Pat. Nos. 3,454,196 and 4,723,687.

U.S. Pat. No. 4,723,687 to Kutterer discloses a cap having a cutting structure for cutting the entire disk-shaped membrane from the container neck. This can provide a relatively large opening within the container neck. However, in some applications, it may be desirable to provide a very small dispensing orifice having a controlled diameter for uniformly dispensing a very fine stream or small drops of liquid. Thus, it would be desirable to provide an improved system in which such a controlled dispensing orifice could be readily provided in a closure membrane.

U.S. Pat. No. 3,454,196 to Hazard discloses a cap having a plug 42 for rupturing a diaphragm seal in a container nozzle or spout. Although the rupturing of the diaphragm forms a dispensing opening, it would be desirable, in some applications, to insure that the opening has a controlled, predetermined diameter for dispensing a fine stream or uniform drops of liquid from the container.

Further, it would also be desirable to provide an improved opening system in which a dispensing orifice can be created with improved, and predictable, flow characteristics. It would be particularly advantageous if the components of such an improved system could be readily manufactured in a substantially uniformly consistent manner within dimensional tolerances sufficient to provide the desired, predetermined dispensing characteristics from container-to-container.

Additionally, it would be beneficial if such an improved system could accommodate the subsequent closing of the open container in a manner that provides a leak-tight seal and that accommodates later reopening and closing.

Further, it would be beneficial if such an improved package could be readily manufactured by conventional, and relatively inexpensive, processes.

The present invention provides system designs that can accommodate one or more of the aforementioned benefits and features.

SUMMARY OF THE INVENTION

One aspect of the present invention includes a dispensing orifice assembly for a sealed container having a liquid contents. The orifice assembly is joined to the container and provides a dispensing orifice of a predetermined size for the container as well as a sealing means. In a preferred embodiment, the orifice size can be precisely controlled. The orifice assembly is particularly suitable for use with a hermetically sealed, thermoplastic container having a boss defining an access port which is sealed by a pierceable membrane. The container contents can be dispensed from the container through the present orifice assembly in a predictable manner. The orifice assembly can be readily manufactured within dimensional tolerances sufficient to maintain the desired dispensing characteristics for the container contents.

The assembly includes a hollow overcap which is mountable on the boss. A metamorphic spike is mounted in, and carried by, the overcap. In a preferred embodiment, this spike includes a piercing pin or lancet having a distal end for penetrating the container membrane and a flange at the other end of the pin. The spike also defines an open, central passageway substantially along its longitudinal axis.

The metamorphic spike is juxtaposed substantially normal to the pierceable membrane when the overcap is mounted to the container but is transferable to the container upon full penetration of the membrane, however. After it has fully penetrated the pierceable container membrane and the overcap is subsequently removed, the metamorphic spike is retained on the container and lines the dispensing orifice of the container as a tubular liner therefor. The liquid contents of the container can then be dispensed through the passageway in the spike as it performs its function as an orifice liner.

In a further preferred embodiment, the overcap can be provided with a trocar or solid pin for extending completely or partially through the dispensing orifice, i.e., the discharge passageway of the hollow spike. The trocar can be designed to aid in piercing the container membrane. In any event, the trocar can function as an orifice sealing member when situated within the passageway. When the overcap is mounted on the container so that the hollow spike fully penetrates the membrane and is retained on the container, the overcap can be removed to withdraw the trocar and permit the contents to be dispensed in a controlled manner through the discharge passageway.

Numerous other advantages and features of the present invention will become readily apparent from the following detailed description of the invention, from the claims, and from the accompanying drawings.

BRIEF DESCRIPTION OF THE DRAWINGS

In the accompanying drawings forming part of the specification, in which like numerals are employed to designate like parts throughout the same.

FIG. 2 is an enlarged, fragmentary, side, elevational view of the assembled components shown in FIG. 1 with the overcap mounted on the container prior to piercing of the container membrane, and FIG. 2 shows portions of the structures broken away to better illustrate interior detail, some of which is shown in cross section;

DESCRIPTION OF THE PREFERRED EMBODIMENTS

The present invention provides an orifice assembly which can be easily installed on a hermetically sealed container to pierce a membrane on the container. The assembly provides a dispensing orifice of a predetermined size. The orifice can be relatively small so that the liquid contents can be discharged from the container in a relatively fine stream. The orifice assembly can be readily manufactured in a substantially uniformly consistent manner within dimensional tolerances sufficient to maintain the desired dispensing characteristics.

While this invention is susceptible of embodiment in many different forms, this specification and the accompanying drawings disclose only some specific forms as examples of the invention. The invention is not intended to be limited to the embodiments so described, and the scope of the invention will be pointed out in the appended claims.

For ease of description, the orifice assembly of this invention is described with reference to a container in an upright, non-dispensing position, and terms such as upper, lower, horizontal, etc., are used with reference to this position. It will be understood, however, that the package of this invention may be stored, transported, and sold in an orientation other than the position described.

The components of this invention may be fabricated and assembled with conventional molding apparatus and other mechanisms, the details of which, although not fully illustrated or described, will be apparent to those having skill in the art and an understanding of the necessary functions of such apparatus and mechanisms. The detailed descriptions of such apparatus or other mechanisms are not necessary to an understanding of the invention and are not herein presented because such apparatus and other mechanisms form no part of the present invention.

A first type of orifice assembly and container which form a package embodying the present invention are illustrated in FIGS. 1–4. The container is designated generally by the reference numeral 10 (FIG. 1), and the two-piece orifice assembly includes a metamorphic, hollow, flanged spike and orifice liner 16 which is adapted to be initially mounted in, and carried by, an overcap 20. Once installed into the container, the hollow spike defines a dispensing orifice for the container contents.

The container 10 is initially molded and filled as a unitary, hermetically sealed structure. The commonly assigned U.S. Pat. Nos. 4,258,867 and 4,671,763 to Weiler et al. describe suitable container fabrication processes in which a container is formed, filled with a liquid, and then sealed, all under continuous, commercial scale, high speed, sterile, manufacturing conditions.

The container 10 includes a hollow body portion 22 in which the thickness of the wall or walls can vary from one location to another. The wall is preferably formed as thin as practical, consistent with structural strength requirements. Preferably, the body wall is sufficiently flexible and resilient so that it can be squeezed to dispense the container contents through an opening that is provided as explained in detail hereinafter.

Figure 1:
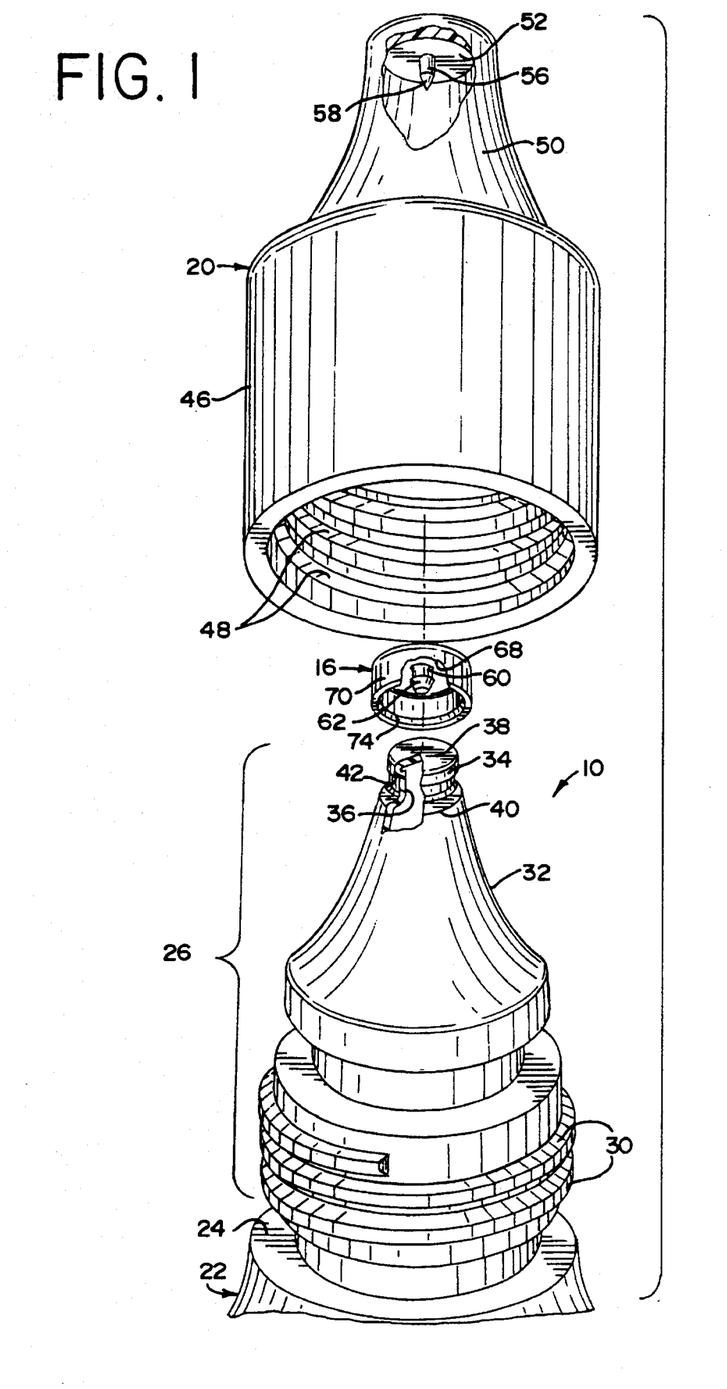
FIG. 1 is an exploded, fragmentary, perspective view of an embodiment of an orifice assembly of the present invention for use with a hermetically sealed container.
Figure 2:
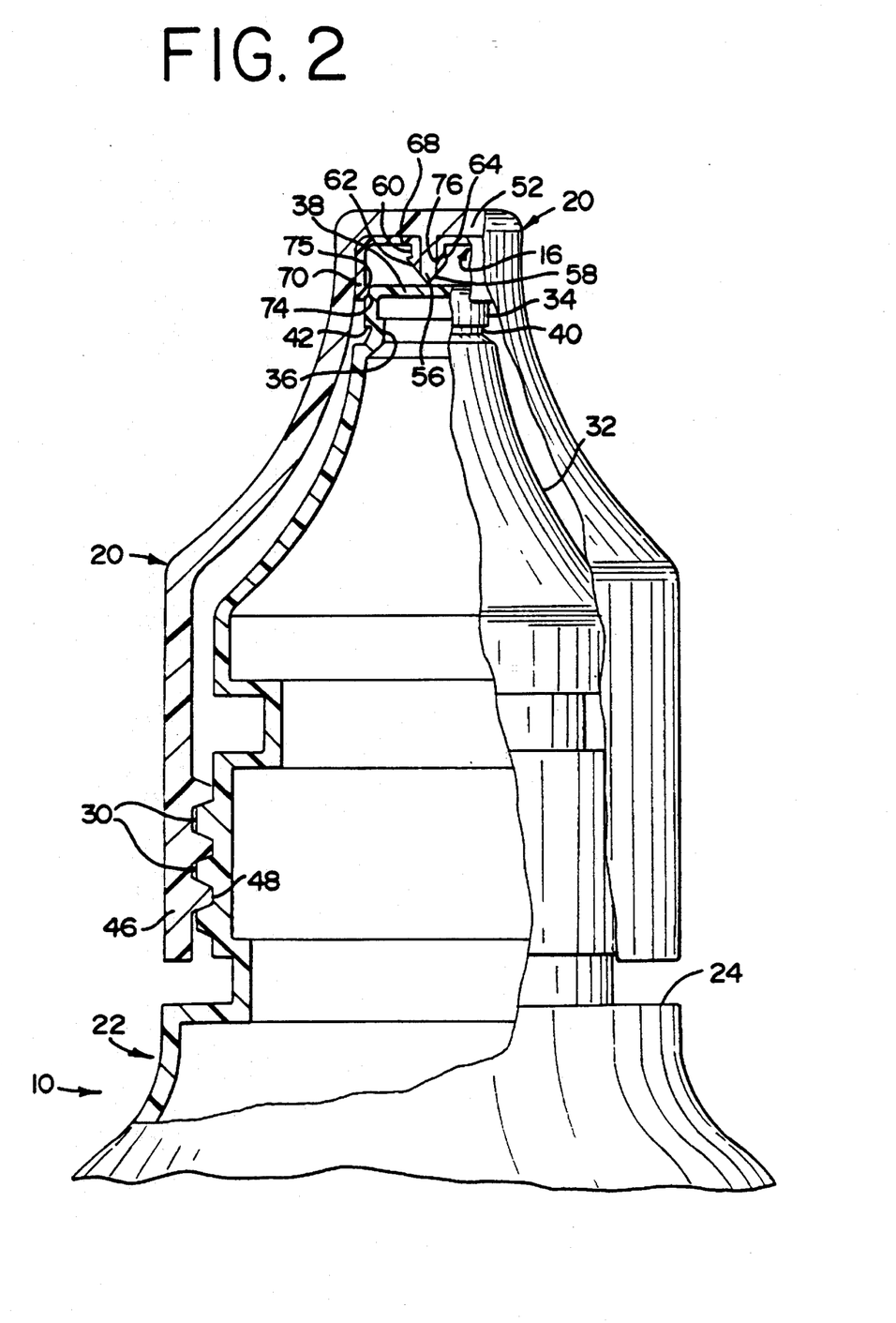

The container body 22 terminates in an upwardly facing, flat, annular flange 24. The container 10 further includes a dispensing end or neck 26 extending outwardly from the shoulder 24. As illustrated in FIG. 2, the container neck 26 includes external threads 30, an outwardly concave nozzle portion 32, and a boss 34 which defines an access port 36. The access port 32 is sealed by a pierceable membrane 38 which closes the dispensing end of the container at the boss 34. Inwardly of the boss 34, the container defines an annular groove or recess 40, and the inner end of the boss 34 defines a downwardly facing, annular shoulder 42.

The container 10 can be molded using a thermoplastic polymer. Presently preferred polymers are low density polyethylene (LDPE), high density polyethylene (HDPE), polypropylene (PP), and the like.

The container 10 may be fabricated by conventional, parison blow-molding processes and apparatuses. Typically, the container 10 is blow-molded in a mold assembly that includes two, coacting, main mold halves defining a split mold cavity to mold the container body 22 and a portion of the container neck 26. Then the molded body is charged with the desired liquid fill.

After the container body is blow-molded in the main mold halves and filled with a desired substance via a filling assembly, a pair of sealing mold halves are closed to complete the molding of the container upper portion, including boss 34 and membrane 38, so as to hermetically seal the contents in the container 10. Such a container molding process, or other suitable variations of it, are well-known and form no part of the present invention.

In the preferred embodiment of the invention, the orifice assembly is employed with a container 10 having a wall thickness and configuration that permits the container, or portions thereof, to be squeezed so as to dispense the container contents through the pierced membrane 38 after access to the container has been provided as described hereinafter.

The overcap 20 and orifice liner 16 are separately formed. The overcap 20 can be made of a relatively rigid, molded, thermoplastic polymer, such as a polystyrene or the like. Such a thermoplastic polymer can be pigmented to contrast with the appearance of the container 10.

In the embodiment illustrated in FIGS. 1–4, the metamorphic, hollow spike and orifice liner 16 is preferably molded from polystyrene or polycarbonate. The hollow spike 16 and overcap 20 can each be separately molded by conventional processes which permit the maintenance of relatively close tolerances and subsequent assembly.

The overcap 20 includes a skirt 46 defining internal threads 48 for engaging the container neck threads 30. Extending upwardly from the overcap skirt 46 is an outwardly concave cover portion 50 which terminates in an end wall 52. A pin or trocar 56 projects from the inside surface of the overcap end wall 52. The pin 56 terminates in a conical point 58.

The metamorphic, hollow spike and liner 16 also has a hollow piercing member, such as a lancet or pin 60, terminating in an open distal end surrounded by a frustoconical surface 62 which defines a barb or steeple head having a rearwardly facing, annular shoulder 64 (FIG. 2). When the hollow spike 16 is inserted in the overcap 20 (FIG. 2), the frustoconical surface 62 of the spike 16 merges with, or forms a relatively smooth continuation of, the trocar conical distal end 58.

Figure 3:
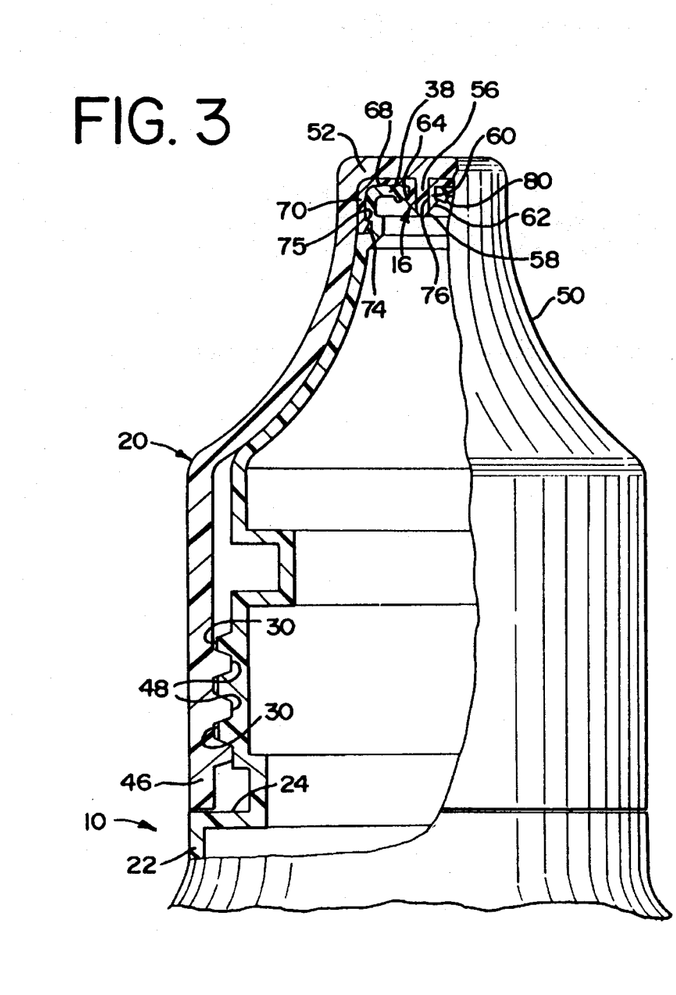
FIG. 3 is a view similar to FIG. 2 and shows the components after the overcap has been fully screwed onto the container to pierce the container membrane.
Figure 4:
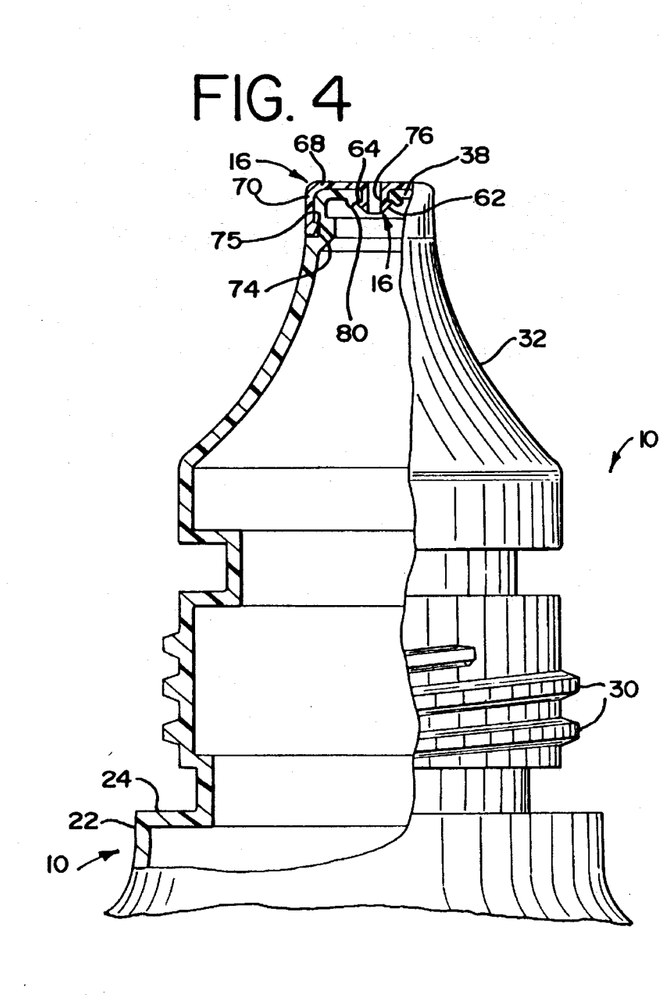
FIG. 4 is a view similar to FIG. 3 and shows the components after the overcap has been completely removed to leave the metamorphic spike and liner in place on the container.
Figure 5:
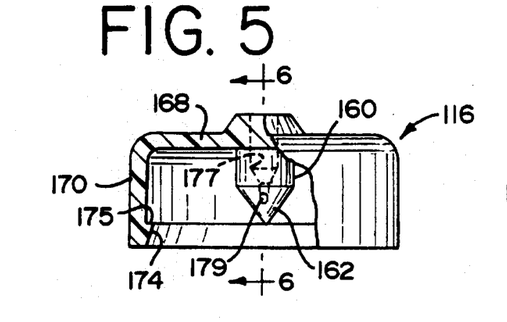
FIG. 5 is a side, elevational view of a further embodiment of spike and liner with portions of the structure cut away to better illustrate interior detail, some of which is shown in cross section.
Figure 6:
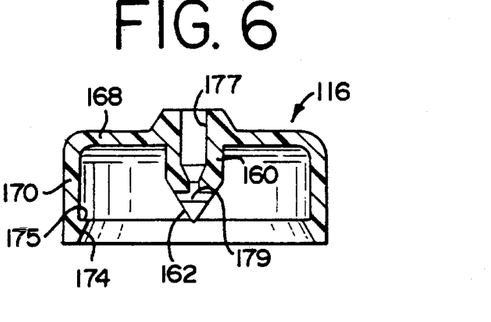
FIG. 6 is a cross-sectional view taken generally along the plane 6—6 in FIG. 5.
Figure 7:
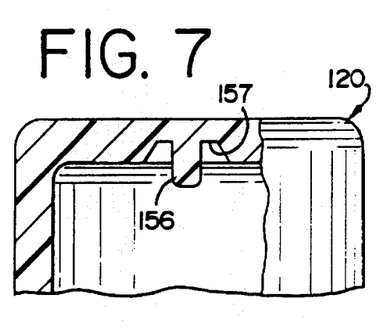
FIG. 7 is a fragmentary, side, elevational view of an overcap for use with the spike and liner illustrated in FIGS. 5 and 6.

The base of the hollow pin 60 is defined by a flange 68. A skirt 70 projects from the periphery of the flange 68, and an annular bead or flange 74 projects radially inwardly from the end of the skirt 70. The bead or flange 74 defines an upwardly facing, annular retaining shoulder 75 (FIGS. 2–4).

The hollow pin 60 defines an internal passageway 76 which is oriented along the longitudinal axis of the pin and which is open at both ends—at the distal end surrounded by the frustoconical surface 62 and at the base flange 68. The passageway 76 is adapted to receive the solid pin or trocar 56.

In the preferred embodiment, the configuration of the passageway 76 is cylindrical. Preferably the diameter of the passageway 76 is carefully controlled during the fabrication process. The passageway 76 may be directly molded to a specified diameter within a low tolerance range, or a smaller diameter passage can be initially molded and subsequently drilled to the precise diameter desired.

The metamorphic spike 16 is adapted to be mounted in, and carried by, the overcap 20 as illustrated in FIG. 2. The liner 16 can be disposed in a friction fit engagement with the interior surface of the overcap 20. The liner 16 may also be retained within the overcap 20 by means of a friction fit between the overcap trocar 56 and the surrounding hollow pin 60. Moreover, or alternatively, the base of the trocar 56 can be provided with an annular groove (not illustrated) for snap fit engagement with a bead (not illustrated) on the interior surface of the liner hollow pin 60. Moreover, other, or additional, retention means may be employed, such as a small amount of adhesive or some other type of snap-fit interlock. However, for reasons that will become clear hereinafter, the metamorphic spike 16 must be releasable from the overcap 20 when the overcap 20 and the spike 16 are subjected to oppositely, directed longitudinal forces which exceed a predetermined maximum value.

The overcap 20 and spike 16 are preferably provided to the user in an assembled condition wherein the spike 16 is initially situated within the overcap 20. The assembly of the overcap 20 and spike 16 are typically packaged along with the container 10. The assembly of the overcap 20 and liner 16 need not be initially mounted on the container neck 26, however.

The container 10 is provided to the user with the assembly of the spike 16 and overcap 20 initially mounted on the container 10 as illustrated in FIG. 2. In that condition, the overcap skirt 46 is threadingly engaged with the container neck threads 30, but only so that the conical distal end 58 of the trocar 56 is spaced from, or merely is resting on, the membrane 38, but has not punctured or pierced the membrane 38.

More preferably, however, when the assembly of the overcap 20 and spike 16 is initially mounted on the container neck as illustrated in FIG. 2, the liner bead or flange 74 at the bottom of the skirt 70 engages the periphery of the boss 34 around the top of the membrane 38. This engagement interferes with continued axial travel of the overcap 20 on the container 10 as thread engagement between the overcap and container neck continues. The interference is felt as increased resistance to further threading of the components. This tactile sensation serves as an indication that further axial advance of the overcap 20 onto container neck threads 30 will begin to effect a piercing of the container membrane 38. As the overcap 20 is advanced further onto the container 10 to pierce the container membrane 38, the overcap 20, hollow spike 16, and/or boss 34 deform as necessary to accommodate movement of the liner bead 74 downwardly along side the boss 34 until the bead 74 is received within the container recess 40 below the boss shoulder 42 as shown in FIG. 3.

The further advance of the overcap 20 onto the container 10 opens the container 10. Typically, the user holds the container 10 and rotates the overcap 20 to increase the threaded engagement between the overcap 20 and the container neck 26. As the bottom of the overcap 20 approaches the shoulder 24 on the container 10, the piercing pin or trocar 56 in the overcap 20 pierces the membrane 38 as illustrated in FIG. 3.

As the overcap 20 moves further toward the container body 22, the opening in the membrane 38 is enlarged and deformed. Upset portions 80 (FIGS. 3 and 4) of the membrane 38 are formed around the opening adjacent the hollow pin 60. When the overcap 20 is fully threaded onto the container 10 as shown in FIG. 3, the enlarged, frustoconical surface 62 of the hollow spike 16 has been forced through the membrane 38 and past the adjacent portions of the upset portions 80. Owing to the somewhat resilient nature of the thermoplastic material from which the container, and hence diaphragm 38, has been molded, the upset portions 80 return radially inwardly somewhat over the retaining shoulder 64. Further, the bead or flange 74 at the end of the liner skirt 70 snaps into place in the recess 40 of the container neck below the shoulder 42 at the lower end of the boss 34. The engagement between the liner pin shoulder 64 and the membrane 38, along with the engagement between the liner flange shoulder 75 and the boss shoulder 42, function to secure the liner 16 to the container 10 and provide a double leak-tight sealing system.

When it is desired to dispense a portion of the contents from the container 10, the overcap 20 is removed by unthreading it from the container neck 26. The removal force is sufficient to overcome the relatively small engagement forces between the liner 16 and overcap 20. However, the hollow spike 16 is securely held by its engagement with the container 10, and is prevented by this engagement from being lifted up from the container membrane 38 as the overcap 20 is disengaged. In this configuration the hollow spike 16 functions as a liner for a dispensing aperture having a predetermined size.

The overcap 20 can be completely disengaged to leave the hollow spike 16 on the container 10 as shown in FIG. 4. When the overcap 20 is completely removed from the container 10 and spike 16, the lined passageway 76 is open, and the contents can be dispensed from the container 10 through the passageway 76. Typically, this is effected by tilting or tipping the container 10 so as to point generally downwardly. The generally flexible resilient walls of the container 10 are then squeezed to effect a discharge of the liquid contents in a fine stream or in small drops. Because the passageway 76 has been formed in a controlled manner during the manufacture of the metamorphic spike 16, the passageway 76 functions as a precisely controlled dispensing orifice regardless of the particular configuration and size of, and irregularities in, the puncture opening formed in the membrane 38.

Preferably, when the metamorphic spike 16 has been driven into the proper piercing relationship and the overcap 20 subsequently removed (FIG. 4), the outwardly concave surface 32 of the container neck portion merges with, and matches, the exterior surface of the liner skirt 70 to provide an aesthetically pleasing assembly.

If only a portion of the container contents is dispensed, the container may be reclosed or resealed by threading the overcap 20 back onto the container 10 so as to occlude the dispensing passageway 76 with the overcap or its trocar 56 (as shown in FIG. 3).

Figure 8:
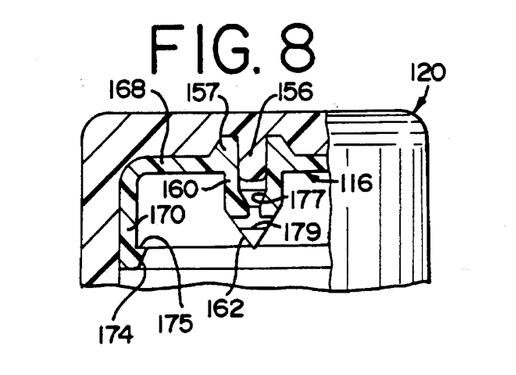
FIG. 8 is a fragmentary, side, elevational view of the spike and liner shown in FIGS. 5 and 6 mounted in the overcap shown in FIG. 7 with portions of the structures cut away to better illustrate interior detail, some of which is shown in cross section.

Another embodiment of a metamorphic, flanged spike and liner is illustrated in FIGS. 5–8 and is designated generally therein by the reference numeral 116. An overcap 120 (FIGS. 7 and 8) is provided for receiving the liner 116 as shown in FIG. 8.

The overcap 120 can be generally similar to the overcap 20 described above with reference to the embodiment illustrated in FIGS. 1–4, and can be provided with threads (not illustrated) for engaging mating threads on a container (not illustrated but similar to the container 10 described above with reference to FIGS. 1–4).

The overcap 120 includes a downwardly projecting pin or trocar 156 having a blunt distal end. A region around the base of the trocar 156 is recessed to define a groove 157.

The metamorphic spike and liner 116 includes a hollow pin 160 having a conical distal end surface 162. The hollow pin 160 extends downwardly from an end wall or flange 168. A skirt 170 extends from the periphery of the flange 168. At the end of the skirt there is an annular flange or bead 174 defining a retaining shoulder 175. The shoulder 175 is adapted to engage a downwardly facing, annular shoulder (not shown) on the container neck portion, such as the shoulder 42 described above with reference to the container 10 illustrated in FIG. 2.

The hollow pin 160 defines a discharge passageway that includes a first passage 177 which extends from the exterior of the liner 116 to an interior portion of the pin 160. A second passage 179 extends at an angle from the end of the first passage 177 to the exterior of the pin 160. More particularly, the second passage 179 is a generally cylindrical bore oriented so that it is perpendicular to, and intersects, a reduced diameter bore region of the first passage 177. The second passage 179 is open at opposite ends on the pin distal end conical surface 162.

The overcap 120 and metamorphic spike 116 are normally furnished in the assembled condition illustrated in FIG. 8. The assembly can be threadingly engaged with a container in the same manner as explained above with respect to the overcap 20, spike and liner 16, and container 10 illustrated in FIGS. 2 and 3. The second embodiment of the liner 116 illustrated in FIG. 8 does not have a steeple head or barb to penetrate, and be retained by, the container membrane. Thus, the spike and liner device 116 is retained on the container solely by the skirt portion retaining shoulder 175 engaging a complementary mating shoulder on the container.

The overcap trocar or pin 156 does not extend completely to the end of the passageway 177 in the liner hollow pin 160. Instead, the blunt end of the trocar 150 terminates within the hollow pin 160. The puncturing of the container membrane is effected solely by the point or conical surface 162 on the distal end of the liner pin 160.

After the overcap 120 has been fully threaded onto the container to establish the proper engagement of the metamorphic spike 116 with the container neck and to effectively puncture the container membrane, the overcap 120 can be unscrewed from the container. This manipulation, of course, removes the trocar 156 from the liner hollow pin 160. The contents of the container 10 can then be dispensed through the second passage 179 and first passage 177. As in the first embodiment, the second embodiment liner passageway (defined by the first passage 177 and second passage 179) can be molded or otherwise provided with a carefully controlled configuration and dimensions so as to permit the container contents to be dispensed through the liner 116 in a controlled, fine stream or small drops.

Figure 9:
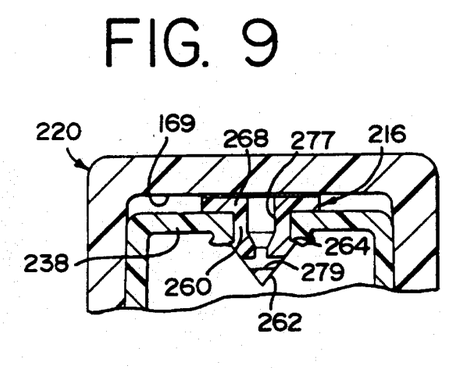
FIG. 9 is a fragmentary, cross-sectional view of another embodiment of an orifice assembly shown penetrating the membrane of a container.

FIG. 9 illustrates a further embodiment of an overcap 220 and a metamorphic, flanged spike and liner 216. The overcap 220 has no pin or trocar and defines a generally flat, interior, sealing end surface 169. The metamorphic spike 216 is initially adhesively secured to the interior surface 169 of the overcap 220.

The metamorphic spike 216 has a base flange 268 and a hollow, piercing pin 260. The distal end of the piercing pin 260 terminates in an enlarged, steeple head having a conical surface 262 forming a barb with an upwardly facing, annular retention shoulder 264.

The liner hollow pin 260 has a discharge passageway defined by a first passage 277 and a second passage 279. The first passage 277 is longitudinally oriented along a portion of the length of the pin 260, and the second passage 279 is oriented to intersect, and be perpendicular to, a reduced diameter portion of the first passage 277. The second passage 279 is a cylindrical bore having opposite ends open at the conical surface 262 of the distal end of the pin 260. The assembly of the metamorphic spike 216 and overcap 220 is threaded onto a container to pierce the container membrane 238 as shown in FIG. 9. In this manner the liner barb shoulder 264 passes beyond part of the deformed portion of the membrane 238 to retain the metamorphic spike 216 on the container. When the overcap 220 is subsequently removed from the container, the overcap unscrewing force is greater than the adhesive strength between the overcap 220 and the liner 216. The overcap 220 can thus be removed completely from the container while leaving the metamorphic spike 216 retained within the container membrane 238 to define a controlled dispensing orifice for dispensing the container contents in the desired, controlled stream or drops.

Figure 10:
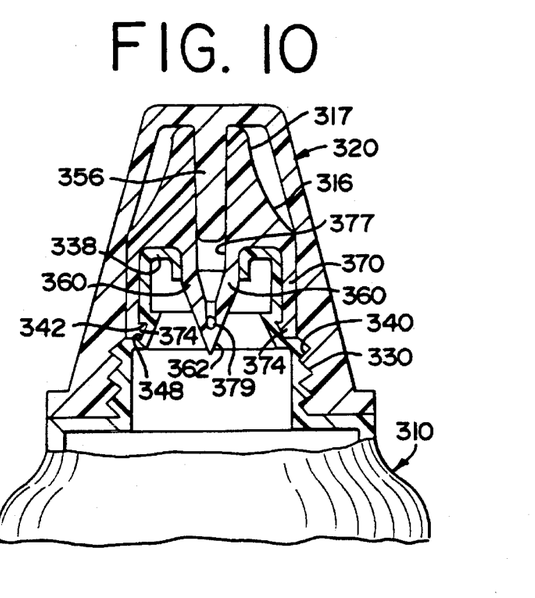
FIG. 10 is a fragmentary, side, elevational view partially cut away to show in cross section yet another embodiment of an orifice assembly mounted on a container and piercing the container membrane.

FIG. 10 illustrates yet another embodiment of an overcap 320 with a metamorphic, flanged spike and liner 316 mounted on a container 310. The container 310 has a neck portion with threads 330 for engaging threads 340 on the interior of the overcap 320.

The metamorphic spike 316 is frictionally, or otherwise, initially retained in a releasable manner in the interior of the overcap 320. The spike 316 has an "eye dropper" configuration with an outwardly concave distal end portion 317. Projecting downwardly from the portion 317 is a skirt 370 having a radially inwardly directed bead or flange 374 for snap-fit engagement with a recess 348 defined below a downwardly facing shoulder 342 in the neck of the container 310.

The spike 316 also includes a hollow pin 360 which terminates in a pointed, conical, distal end surface 362. A first passage 377 extends from the upper end of the liner 316 into the pin 360 and terminates in an intersecting, perpendicular second passage 379. The second passage 379, in the preferred embodiment, is a cylindrical bore having a controlled diameter which is open at opposite ends on the conical surface 362.

The overcap 320 includes a solid pin or trocar 356 for entering into the liner first passage 377 in a leak-tight, sealing engagement. As illustrated in FIG. 10, the overcap 320, with the metamorphic spike 316 mounted therein, can be threaded onto the container 310 to puncture the container membrane 338. When sufficient threaded engagement has been established between the overcap 320 and the container 310, the membrane 338 is fully pierced and the liner skirt bead 374 becomes engaged with the container shoulder 342 near the top of the container 310 so as to prevent removal of the metamorphic spike 316. When the overcap 320 is subsequently unscrewed from the container 310, the frictional fit, or other engagement, between the spike 316 and overcap 320 is overcome. The overcap 320 then separates from the spike 316 which remains embedded in the container 310 while defining a dispensing orifice therein.

The contents can be dispensed from the open container 310 in a controlled manner through the liner passages 379 and 377. The container 310 can be resealed by reapplying the overcap 320 to occlude the liner first passage 377 with the trocar or pin 356.

It will be readily apparent from the foregoing detailed description of the invention and the illustrated embodiments thereof that numerous other variations and modifications may be effected without departing from the true spirit and scope of the novel concepts or principles of this invention.

What is claimed is:

1. A dispensing orifice assembly providing a dispensing orifice of a predetermined size for a container having an access port thereto defined by a boss and sealed by a pierceable membrane, which assembly comprises:

a hollow overcap mountable on said boss; and a metamorphic flanged spike in said overcap and juxtaposed substantially normal to said pierceable membrane when the overcap is mounted to said container and transferable to said container upon full penetration of said membrane, said spike defining therein an open central passageway for container access substantially along the longitudinal axis of the spike when retained on said container.

2. The assembly in accordance with claim 1 in which said spike terminates at the distal end thereof in a steeple head for retaining the spike in place on the container.

3. The assembly in accordance with claim 1 in which said spike passageway extends completely through from one end of the spike to the other; and said overcap includes a projecting trocar extending through said spike passageway.

4. A dispensing orifice assembly providing a dispensing orifice of a predetermined size for a container having an access port thereto defined by a boss and sealed by a pierceable membrane, which assembly comprises:

a hollow overcap mountable on said boss; and a metamorphic flanged spike in said overcap and juxtaposed substantially normal to said pierceable membrane when the overcap is mounted to said container and transferable to said container upon full penetration of said membrane, said spike defining therein an open central passageway for container access substantially along the longitudinal axis of the spike that extends completely through from one end of the spike to the other when retained on said container, said overcap includes a projecting trocar extending through said spike passageway, said trocar has a conical distal end; and said spike has an open distal end surrounded by a frustoconical surface whereby said trocar conical distal end merges with said frustoconical surface.

5. The assembly in accordance with claim 1 in which said spike includes a hollow piercing pin having a conical distal end and a flange at the other end;

said pin conical distal end defines a conical piercing surface; and said spike passageway includes (1) a first passage extending from the flange end of said pin and terminating within said pin and (2) a second passage extending at an angle from the end of said first passage to the exterior of said pin at said conical piercing surface.

6. The assembly in accordance with claim 1 in which said spike is disposed in a friction fit engagement with said overcap.

7. A dispensing orifice assembly providing a dispensing orifice of a predetermined size for a container having an access port thereto defined by a boss and sealed by a pierceable membrane, which assembly comprises:

a hollow overcap mountable on said boss; and a metamorphic flanged spike in said overcap and juxtaposed substantially normal to said pierceable membrane when the overcap is mounted to said container and transferable to said container upon full penetration of said membrane, said spike defining therein an open central passageway for container access substantially along the longitudinal axis of the spike when retained on said container, said spike flange is at one end, a skirt projecting from the periphery of said flange, and an annular flange at the end of said skirt projecting radially inwardly to effect a snap-fit engagement with a shoulder on said container.

8. A package suitable for dispensing a substance, said package comprising:

a container terminating in a closed dispensing end defining a pierceable membrane;

an overcap positioned over said container dispensing end; and a tubular liner means releasably carried initially in said overcap for mounting on said container dispensing end after a predetermined amount of relative axial displacement is effected between said container and said overcap, said liner means including retention means for engaging said container dispensing end to retain said liner means thereon upon subsequent removal of said overcap, said liner means including a projecting insertion means for penetrating said membrane as said predetermined amount of relative axial displacement is effected, and said liner means defining a discharge passageway that has a predetermined configuration and that extends through said insertion means for dispensing the container contents after said overcap has been removed.

9. The package in accordance with claim 8 in which said liner means includes a piercing pin with a flange;

said pin defines said insertion means;

said pin is hollow and defines said discharge passageway; and said overcap includes a projecting trocar for extending through said discharge passageway.

10. A package suitable for dispensing a substance, said package comprising:

a container terminating in a closed dispensing end defining a pierceable membrane;

an overcap positioned over said container dispensing end; and a tubular liner means releasably carried initially in said overcap for mounting on said container dispensing end after a predetermined amount of relative axial displacement is effected between said container and said overcap, said liner means including retention means for engaging said container dispensing end to retain said liner means thereon upon subsequent removal of said overcap, said liner means including a projecting insertion means for penetrating said membrane as said predetermined amount of relative axial displacement is effected, and said liner means defining a discharge passageway that has a predetermined configuration and that extends through said insertion means for dispensing the container contents after said overcap has been removed, said liner means includes a piercing pin with a flange;

said pin defines said insertion means;

said pin is hollow and defines said discharge passageway said overcap includes a projecting trocar for extending through said discharge passageway;

said trocar has a conical end; and said pin is in the form of a hollow cannula with an open distal end surrounded by a frustoconical surface whereby said trocar conical end merges with said frustoconical surface when said liner is releasably carried in said overcap.

11. A package suitable for dispensing a substance, said package comprising:

a container terminating in a closed dispensing end defining a pierceable membrane;

an overcap positioned over said container dispensing end; and a tubular liner means releasably carried initially in said overcap for mounting on said container dispensing end after a predetermined amount of relative axial displacement is effected between said container and said overcap, said liner means including retention means for engaging said container dispensing end to retain said liner means thereon upon subsequent removal of said overcap, said liner means including a projecting insertion means for penetrating said membrane as said predetermined amount of relative axial displacement is effected, and said liner means defining a discharge passageway that has a predetermined configuration and that extends through said insertion means for dispensing the container contents after said overcap has been removed, said container includes an annular shoulder adjacent said dispensing end;

said liner means includes a flange with a peripheral skirt; and said retention means includes a resilient, annular flange that is located at the end of said skirt and that extends radially inwardly to effect a snap-fit engagement with said container shoulder.

12. The package in accordance with claim 8 in which said liner insertion means includes a hollow pin having an open distal end; and said retention means includes a barb adjacent said open distal end for passing through said membrane and then engaging said membrane on the inside of said container to prevent removal of said liner.

13. The package in accordance with claim 8 in which said liner insertion means includes a pointed, projecting pin; and said discharge passageway includes a first passage extending from the exterior of said liner means to an interior portion of said pin and includes a second passage extending at an angle from the end of said first passage to the exterior of said pin.

14. The package in accordance with claim 8 in which said dispensing end of said container includes an externally threaded neck; and said overcap includes an internally threaded skirt for engaging said container neck whereby a relative rotational threading movement between said neck and overcap drives said insertion means through said membrane.

15. The package in accordance with claim 8 in which said container is a unitary, blow-molded, hermetically-sealed bottle having a flexible, hollow body defined in part by a resilient side wall for being squeezed to expel the container contents in a substantially uniform discharge as drops or a continuous stream.

16. The package in accordance with claim 8 in which said overcap has a receiving cavity; and said liner means is disposed in said receiving cavity in a friction fit engagement with said overcap.

* * * * *